United States Patent [19]

Frankel et al.

[11] Patent Number: 4,900,851
[45] Date of Patent: * Feb. 13, 1990

[54] SYNTHESIS OF AZIDODINITRO COMPOUNDS

[75] Inventors: Milton B. Frankel, Tarzana; James F. Weber, Moorpark, both of Calif.

[73] Assignee: The United States of America as represented by the Secretary of the Air Force, Washington, D.C.

[*] Notice: The portion of the term of this patent subsequent to Jan. 3, 2006 has been disclaimed.

[21] Appl. No.: 82,879

[22] Filed: Aug. 5, 1987

[51] Int. Cl.$^4$ .................... C07C 117/00; C06B 25/00; C25B 3/00
[52] U.S. Cl. ........................................ 552/12; 204/72; 149/88
[58] Field of Search ............... 204/72, 57 R; 260/349; 568/704; 149/88; 552/12

[56] References Cited

U.S. PATENT DOCUMENTS

| | | | |
|---|---|---|---|
| 3,356,714 | 12/1967 | Kamlet | 149/88 |
| 3,770,795 | 11/1973 | White | 149/88 |
| 3,883,377 | 5/1975 | Wright | 204/72 |
| 4,472,311 | 9/1984 | Frankel et al. | 260/349 |
| 4,795,593 | 1/1989 | Frankel et al. | 204/72 |

OTHER PUBLICATIONS

Chemical Abstract 35191q vol. 69, No. 9 1968 Slovetskii, V. I. et al.
Chemical Abstract 65882r vol. 73, No. 13 1970 Tselinskii et al.
Organic Chemistry 3rd ed. Morrison et al., Allyn and Bacon, Boston 1973.

*Primary Examiner*—John F. Niebling
*Assistant Examiner*—Steven P. Marquis
*Attorney, Agent, or Firm*—Charles E. Bricker; Donald J. Singer

[57] ABSTRACT

Provided herein are the compounds 4,4-dinitro-1-butanol, 4-azido-4,4-dinitro-1-butyl acetate and methods for preparing each compound.

4,4-dinitro-1-butanol is prepared by reacting trinitromethane with acrolein, reducing the resulting trinitroaldehyde to provide the corresponding alcohol and reducing the alcohol.

4-azido-4,4-dinitro-1-butyl acetate is prepared by reacting 4,4-dinitro-1-butanol with acetyl chloride to yield the corresponding acetate and reacting the acetate with an alkali metal azide in an electrolysis cell.

2 Claims, No Drawings

4,900,851

SYNTHESIS OF AZIDODINITRO COMPOUNDS

RIGHTS OF THE GOVERNMENT

The invention described herein may be manufactured and used by or for the Government of the United States for all governmental purposes without the payment of any royalty.

BACKGROUND OF THE INVENTION

This invention relates to energetic organic compounds. In one aspect, this invention relates to gem-dinitro precursor alcohols. In another aspect, it relates to azidodinitro compounds. In a further aspect, it relates to methods for preparing these compounds.

Energetic organic compounds have a long history of use in explosives and propellants. Examples have included polynitroaromatic compounds such as 2,4,6-trinitrotoluene (TNT); cyclic nitramines such as 1,3,5-trinitrazacyclohexane (RDX) and 1,3,5,7,- tetranitrazacyclooctane (HMX); and nitrate esters such as nitrocellulose (NC) and nitroglycerin (NG). Despite some shortcomings in terms of their thermal stability and sensitivity, these materials have seen heavy use during the past century.

More recently, considerable attention has been paid to various polynitro aliphatic compounds. Compounds, such as bis(2,2-dinitropropyl) formal/acetal (BDPNF-A) and bis(2,2,2-fluoridinitroethyl) formal (FEFO), have found widespread use as energetic plasticizers in modern explosive and propellant formulations.

Yet another promising class of compounds is the group of azido and azidonitro aliphatic compounds. Despite their well deserved reputation as sensitive materials, organic azides are potentially useful ingredients in energetic formulations because the azido group contributes 80 to 90 kcal/mol, while not detracting from the O/C ratio of the molecule. Incorporating both azido and polynitro functionalities in the same molecule generally has been accomplished by joining individual polynitroalkyl and azidoalkyl moieties via a non-energetic linkage. Examples include azidoalkyl esters of polynitroacids such as 1,3-diazido-2-propyl 4',4',4'-trinitrobutyrate (DAPT) and azide-terminated nitramines such as 1,7-diazido-2,4,6-trinitrazeheptane (DATH) and 1,5-diazido-3-nitrazapentene (DANPE). A more compact combination of these two functionalities would be the use of the azidodinitromethyl group in place of trinitromethyl and fluorodinitromethyl groups, which have been incorporated previously in propellant ingredients.

It is an object of the present invention to provide novel azidodinitro compounds.

It is another object of this invention to provide a method for preparing novel azidodinitro compounds.

It is yet another object of this invention to provide novel gem-dinitro alcohols.

It is a further object of this invention to provide a method for preparing gem-dinitro alcohols.

Other objects, aspects and advantages of the present invention will be readily apparent to those skilled in the art from a reading of the following detailed disclosure.

SUMMARY OF THE INVENTION

In accordance with the present invention there is provided the compound 4,4-dinitro-1-butanol and a method for making same which comprise reacting trinitromethane and acrolein at a reduced temeprature to provide 4,4,4-trinitrobutyraldehyde, reducing the butyraldehyde to provide the corresponding alcohol, and reducing the alcohol.

Also provided is the compound 4-azido-4,4-dinitro-1-butyl acetate and a method for preparing same which comprises reacting 4,4-dinitro-1-butanol with acetyl chloride to provide the corresponding ester, and reacting the ester with an alkali metal azide in the electrolysis cell.

There is further provided the compound 4-azido-4,4-dinitro-1-butanol and a method for preparing same which comprises reacting 4-azido-4,4-dinitro-1-butyl acetate with methanol and recovering the aforesaid azidodinitro alcohol.

DESCRIPTION OF THE PREFERRED EMBODIMENTS 4,4-dinitro-1-butanol is prepared according to the scheme shown below.

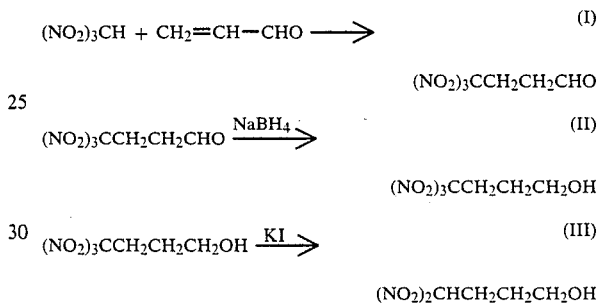

The addition of trinitromethane to acrolein (Reaction I) is conducted at a temperature of about −10° to +10° C. in aqueous medium. Stoichiometric quantities may be employed, although it is presently preferred to employ a slight excess of acrolein. After the addition is complete, the solution may be allowed to warm to room temperature. The organic phase is separated from the aqueous phase and the aqueous phase is extracted with a suitable solvent, such as, for example, methylene chloride. The combined organic layers are washed with water, separated, dried and concentrated to yield the aldehyde.

The reduction of the aldehyde to 4,4,4-trinitro-1-butanol (Reaction II) is conducted at a reduced temperature of about 0° to 10° C. in alcoholic solution by the portionwise addition of sodium borohydride to the aldehyde solution. After the addition is complete, the solution may be allowed to warm to room temperature. The solution may be stirred for 2 to 12 hours to ensure complete reaction. Following removal of the solvent, the remaining material is hydrolyzed with a suitable acid, then extracted with a suitable solvent, such as methylene chloride. The extracts are washed successively with water, a weak basic solution and water, then dried and concentrated to yield the trinitroalcohol.

The conversion of 4,4,4-trinitro-1-butanol to 4,4-dinitro-1-butanol (Reaction III) is conducted by stirring the trinitro alcohol is a suitable alcoholic medium with an excess of KI at room temperature for 1 to 10 days or about 2 to 24 hours at an elevated temperature. The precipitated potassium salt is filtered. suspended in water, acidified, and then extracted with a suitable organic solvent. The extracts are neutralized, dried and concentrated to yield the dinitro alcohol.

The azidodinitro compounds of this invention are prepared according to the following scheme.

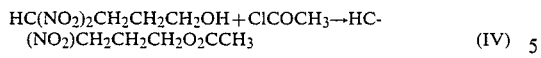

(IV)

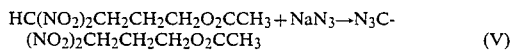

(V)

The 4,4-dinitro-1-butyl acetate is prepared (Reaction IV) by treating a solution of 4,4-dinitro-1-butanol in a suitable solvent, such as methylene chloride, with about 10 to 30 percent excess acetyl chloride. After complete addition of the acetyl chloride, the resulting mixture is stirred at room temperature for 30 to 120 minutes. The mixture is then quenched with cooled water, separated, dried and concentrated to yield the desired dinitro acetate.

Conversion of the 4,4-dinitro-1-butyl acetate to the correspondingazido dinitro compound (Reaction V) is accomplished by charging the dinitro compound together with aqueous sodium azide and an electrolyte, such as NaOH, to the anode compartment of a divided electrolysis cell, charging aqueous soidum azide to the cathode compartment of the cell and applying a current to the cell. After a suitable reaction period, the reaction is stopped and the anolyte extracted with a suitable solvent, such as methylene chloride. The extract is then washed, dried and concentrated to yield the desired product.

The following examples illustrate the invention.

EXAMPLE I

4,4,4-Trinitrobutyraldehyde

A 12 L three-necked, round-bottom flask with a thermometer, mechanical stirrer, and 1000 ml addition funnel was charged with 6377 g of an 11% aqueous trinitromethane solution (701.5 g; 4.675 mol) and cooled in a dry-ice bath at 9° C. A solution of acrolein (274.1 g, 4.90 mol) in 2000 ml of water was added at a rate that maintained the temperature at 0° C. The dry-ice bath was removed and the stirred solution allowed to warm to room temperature overnight. The two phases were separated and the aqueous layer was extracted with $CH_2Cl_2$ (2×2000 ml). The combined organic layers were washed with water (2×2000 ml). The product was dried ($MgSO_4$) and concentrated to give 878 g (91%) of the aldehyde as a yellow oil; $n_D = 1.4731$ (26C). The infrared spectrum showed bands at 1725 $cm^{-1}$ (C=O), 1590, 1300, and 800 $cm^{-1}$ ($NO_2$).

EXAMPLE II

4,4,4-trinitro-1-Butanol

Crude 4,4,4-trinitrobutaldehyde (878 g, 4.24 mol) was dissolved in methanol (1000 ml) and cooled in an ice bath while $NaBH_4$ (130.7 g, 3.44 mol) was added portion-wise. The mixture was stirred at room temperature overnight under a nitrogen purge which removed much of the solvent. The thick suspension was hydrolyzed with 6 N HCl (approx. 4l) and the product extracted with $CH_2Cl_2$ (3×1000 ml). The extracts were washed with water (1000 ml), saturated $NaHCO_3$ (2×1000 ml), and water (1000 ml). The product solution was dried over anhydrous $MgSO_4$ and concentrated to yield 554 g (63%) of a yellow oil, $n_D = 4735$ (19C). The infrared spectrum showed peaks at 3619, 3370, 2950, 2890, 1595, 1305, 1058 and 801 $cm^{-1}$.

EXAMPLE III

4,4-Dinitro-1-Butanol

This alcohol was prepared by stirring 4,4,4-trinitro-1-butanol (554 g, 2.65 mol) in methanol (6 l) with KI (1426 g, 8.6 mol) for 6 days at room temperature. The precipitated potassium salt was filtered, suspended in water (4 L), acidified with concentrated HCl (250 ml), and extracted into $CH_2Cl_2$ (6×500 ml). The extracts were washed with 10% $NaHSO_3$ (1000 ml). The solution was dried over anhydrous $MgSO_4$ and concentrated to give the product (220 g, 51%) as a yellow oil. The infrared spectrum had peaks at 3450, 2950, 1575, 1340, and 1070 $cm^{-1}$.

EXAMPLE IV

4,4-Dinitro-1-Butyl Acetate

This ester was synthesized by treating a solution of 4,4-dinitro-1-butanol (39.2 g, 0.24 mols) in $CH_2Cl_2$ (100 ml) with acetyl chloride (22 ml, 24 g, 0.31 mol). After 90 minutes at room temperature, the reaction was quenched with ice water. Separation, drying ($MgSO_4$), and concentration of the organic phase gave the product (42.7 g, 87%) as a light yellow oil; $n_D = 1.4574$ (24C). The infrared spectrum of the product had peaks at 2960, 1745, 1575, 1245, and 1060 $cm^{-1}$. Elemental analyses-Calculated for $C_6H_{10}N_2O_6$: C, 34.95; H, 4.85; N, 13.59; Found: C, 35.17; H, 4.83; N, 12.95.

EXAMPLE V

4-Azido-4,4-Dinitro-1-Butyl Acetate

A divided electrochemical H-cell was charged with 4,4-dinitro-1-butyl acetate (10.2 g), 30% aqueous $NaN_3$ (25 ml) and 12N NaOH (4 ml) in the anode compartment and 30% $NaN_3$ (35 ml) in the cathode compartment. This solution was electrolyzed at 650 mA using a platinum foil anode (6.5 $cm^2$) and a stainless steel cathode. After 5.25 h the reaction was stopped, and the anolyte was extracted with $CH_2Cl_2$ (3×25 ml). Brine-washing, drying, and concentrating the extracts yielded a product which displayed a weak hydroxyl absorption in the infrared spectrum. The product was reacetylated by stirring with acetyl chloride (1 ml) in $CH_2Cl_2$ (30 ml) for 2 h. This reaction was quenched in ice water, dried, and concentrated. The crude yellow oil was purified by column chromatography on silica gel eluting with 10% ethyl acetate in hexanes. The purified product was a clear light yellow oil which was greater than 95% pure by HPLC: $n_D = 1.4649$ (25C); IR: 2165, 1735, and 1590 $cm^{-1}$; NMR ($CDCl_3$): 4.07 (q, 2H), 2.58 (m, 2H), 2.07 (s, 3H), 1.73 (m, 2H). Elemental analyses calcluated for $C_6H_9N_5O_6$: C, 29.15; H, 3.64; N, 28.34. Found: C, 29.59; H, 3.90; N, 27.89.

Various modifications may be made without departing from the spirit of the invention or the scope of the appended claims.

We claim:

1. 4-azido-4,4-dinitro-1-butyl acetate.
2. A method for preparing 4-azido-4,4-dinitro-1-butylacetate which comprises electrochemically reacting 4,4-dinitro-1-butanol with acetyl chloride to yield 4,4-dinitro-1-butyl acetate and reacting said acetate with an alkali metal azide in an electrolysis cell.

* * * * *